US010843173B2

(12) United States Patent
Hwang et al.

(10) Patent No.: US 10,843,173 B2
(45) Date of Patent: Nov. 24, 2020

(54) FERRITE CATALYST FOR OXIDATIVE DEHYDROGENATION, METHOD OF PREPARING FERRITE CATALYST, AND METHOD OF PREPARING BUTADIENE USING FERRITE CATALYST

(71) Applicant: LG CHEM, LTD., Seoul (KR)

(72) Inventors: Sun Hwan Hwang, Daejeon (KR); Dong Hyun Ko, Daejeon (KR); Jun Han Kang, Daejeon (KR); Kyong Yong Cha, Daejeon (KR); Joo Hyuck Lee, Daejeon (KR); Hyun Seok Nam, Daejeon (KR); Dae Heung Choi, Daejeon (KR); Myung Ji Suh, Daejeon (KR); Ye Seul Hwang, Daejeon (KR); Jun Kyu Han, Daejeon (KR); Sang Jin Han, Daejeon (KR); Seong Min Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 90 days.

(21) Appl. No.: 16/307,317

(22) PCT Filed: Jan. 4, 2018

(86) PCT No.: PCT/KR2018/000160
§ 371 (c)(1),
(2) Date: Dec. 5, 2018

(87) PCT Pub. No.: WO2018/139776
PCT Pub. Date: Aug. 2, 2018

(65) Prior Publication Data
US 2019/0134612 A1    May 9, 2019

(30) Foreign Application Priority Data

Jan. 26, 2017  (KR) .................. 10-2017-0012545
Dec. 7, 2017   (KR) .................. 10-2017-0167295

(51) Int. Cl.
| *B01J 23/00* | (2006.01) |
| *B01J 23/80* | (2006.01) |
| *B01J 37/08* | (2006.01) |
| *C07C 5/48* | (2006.01) |
| *C07C 11/167* | (2006.01) |
| *B01J 35/10* | (2006.01) |
| *B01J 23/78* | (2006.01) |
| *B01J 23/70* | (2006.01) |
| *B01J 23/745* | (2006.01) |
| *B01J 37/03* | (2006.01) |
| *B01J 21/00* | (2006.01) |
| *B01J 37/00* | (2006.01) |

(52) U.S. Cl.
CPC ............. *B01J 23/80* (2013.01); *B01J 21/005* (2013.01); *B01J 23/00* (2013.01); *B01J 23/70* (2013.01); *B01J 23/745* (2013.01); *B01J 23/78* (2013.01); *B01J 35/1014* (2013.01); *B01J 37/00* (2013.01); *B01J 37/036* (2013.01); *B01J 37/08* (2013.01); *C07C 5/48* (2013.01); *C07C 11/167* (2013.01); *C07C 2523/745* (2013.01); *C07C 2523/80* (2013.01)

(58) Field of Classification Search
CPC ........ B01J 23/80; B01J 23/745; B01J 37/036; B01J 37/08
USPC .......................................... 423/594.1, 594.14
See application file for complete search history.

(56) References Cited

U.S. PATENT DOCUMENTS

| 3,828,101 | A | * | 8/1974 | Miklas | ...................... C07C 5/48 423/594.2 |
| 3,843,745 | A | * | 10/1974 | Christman | ............... B01J 37/03 585/625 |
| 3,849,545 | A | * | 11/1974 | Miklas | ...................... B01J 37/03 423/594.2 |
| 3,872,027 | A | * | 3/1975 | Christmann | ........... B01J 23/745 502/324 |
| 3,937,748 | A | * | 2/1976 | Miklas | ...................... B01J 23/80 585/443 |
| 9,090,470 | B2 | | 7/2015 | Sueki et al. | |
| 2003/0224924 | A1 | | 12/2003 | Satcher, Jr. et al. | |
| 2006/0204764 | A1 | | 9/2006 | Hirao et al. | |
| 2010/0121123 | A1 | | 5/2010 | Chung et al. | |
| 2014/0066680 | A1 | | 3/2014 | Miao et al. | |
| 2016/0184806 | A1 | | 6/2016 | Xiong et al. | |

FOREIGN PATENT DOCUMENTS

| CN | 1202706 | 12/1998 |
| CN | 1066565 | 5/2001 |
| CN | 1765494 | 5/2006 |

(Continued)

OTHER PUBLICATIONS

Extended Search Report of European Patent Office in Appl'n No. 18744568.9, dated Apr. 15, 2020.
International Search Report and the Written Opinion of PCT/KR2018/000160, dated Apr. 13, 2018.
Bhosale et al., "Propylene oxide assisted sol-gel synthesis of zinc ferrite nanoparticles for solar fuel production," Ceramics International 42: 2431-2438 (2016).

(Continued)

Primary Examiner — Steven J Bos
(74) Attorney, Agent, or Firm — Dentons US LLP (57) ABSTRACT

A ferrite catalyst for oxidative dehydrogenation and a method of preparing the same. The ferrite catalyst is prepared using an epoxide-based sol-gel method, wherein a step of burning includes a first burning step, in which burning is performed at a temperature of 70 to 200° C.; and a second burning step, in which burning is performed after the temperature is raised from a temperature in the range of greater than 200° C. to 250° C. to a temperature in the range of 600 to 900° C.

13 Claims, 2 Drawing Sheets

(56) References Cited

FOREIGN PATENT DOCUMENTS

| | | |
|---|---|---|
| JP | S46-20630 | 6/1971 |
| JP | 2855378 | 2/1999 |
| JP | 2010083746 | 4/2010 |
| JP | 2012226916 | 11/2012 |
| JP | 2015167886 | 9/2015 |
| KR | 10-0847206 | 7/2008 |
| KR | 10-1161625 | 7/2012 |
| WO | 2005051864 | 6/2005 |

OTHER PUBLICATIONS

Office Action of Japanese Patent Office in Appl'n No. 2018-563905 dated Nov. 12, 2019.
Bhosale et al., "Propylene oxide assisted sol-gel synthesis of zinc ferrite nanoparticles for solar fuel production," Ceramics International 42(2): 2431-2438 (2016), published online Oct. 23, 2015.
Office Action of Korean Patent Office in Appl'n No. 10-2017-0167295 dated Jun. 26, 2019.

\* cited by examiner

FERRITE CATALYST FOR OXIDATIVE DEHYDROGENATION, METHOD OF PREPARING FERRITE CATALYST, AND METHOD OF PREPARING BUTADIENE USING FERRITE CATALYST

CROSS-REFERENCE OF RELATED APPLICATION

This application is a National Stage Application of International Application No. PCT/KR2018/000160 filed on Jan. 4, 2018, which claims priority to Korean Patent Application No. 10-2017-0012545, filed on Jan. 26, 2017, and Korean Patent Application No. 10-2017-0167295, re-filed on Dec. 7, 2017, based on the priority of the above patent, in the Korean Intellectual Property Office, the disclosures of each of which are incorporated herein by reference.

TECHNICAL FIELD

The present invention relates to a ferrite catalyst for oxidative dehydrogenation, a method of preparing the ferrite catalyst, and a method of preparing butadiene using the ferrite catalyst. More specifically, the present invention relates to a method of preparing a ferrite catalyst for oxidative dehydrogenation having excellent reactivity using an epoxide-based sol-gel method, wherein the ferrite catalyst has a large surface area, a macroporous structure, and a pure spinel phase structure that does not include an $\alpha\text{-}Fe_2O_3$ phase.

BACKGROUND ART

Butadiene, an important basic chemical, is used as an intermediary for various petrochemical products, such as synthetic rubber and electronic materials, and demand and value thereof, as a basic fraction, are gradually increasing in the petrochemical market. Butadiene can be prepared by naphtha cracking, direct dehydrogenation of normal-butene (n-butene), oxidative dehydrogenation of (n-butene), or the like.

Thereamong, according to the method of preparing butadiene by oxidative dehydrogenation of butene, butene reacts with oxygen in the presence of a metal oxide catalyst to generate butadiene and water. In this case, water generated as a result of the reaction is stable. Thus, the reaction is thermodynamically very advantageous. In addition, since oxidative dehydrogenation of butene is an exothermic reaction unlike direct dehydrogenation of butene, 1,3-butadiene may be obtained in a high yield even at low reaction temperature as compared with direct dehydrogenation. Also, the reaction may be performed without additional heat supply. Therefore, when the method using oxidative dehydrogenation of butene is used, increase in demand for 1,3-butadiene may be effectively satisfied.

In general, the metal oxide catalyst is synthesized by a coprecipitation method, which includes precipitation, aging, filtration/washing, drying, and burning steps. Since a synthetic product prepared by the coprecipitation method is composed of small particles, much time is consumed in the filtration/washing step. In addition, in the synthetic product prepared by the coprecipitation method, an $\alpha\text{-}Fe_2O_3$ phase is formed after the burning step. In addition, when the coprecipitation method is used to prepare a catalyst, the catalyst is prepared in bulk form, which may reduce catalytic activity thereof during a catalytic reaction.

PRIOR ART DOCUMENT

[Patent Document](Patent Document 1) JP 2015-167886 A

DISCLOSURE

Technical Problem

Therefore, the present invention has been made in view of the above problems, and it is one object of the present invention to provide a ferrite catalyst for oxidative dehydrogenation having excellent reactivity prepared by an epoxide-based sol-gel method.

It is another object of the present invention to provide a method of preparing the ferrite catalyst for oxidative dehydrogenation and a method of preparing butadiene using the ferrite catalyst.

The above and other objects can be accomplished by the present disclosure described below.

Technical Solution

In accordance with one aspect of the present invention, provided is a method of preparing a ferrite catalyst for oxidative dehydrogenation, including (a) a step, in which a trivalent cationic iron (Fe) precursor and a divalent cationic metal (A) precursor are dissolved in an alcohol solvent to prepare a precursor solution; (b) a step, in which an epoxide compound is mixed with the precursor solution to obtain a gel; (c) a step of aging the obtained gel; (d) a step of obtaining a synthetic product by drying the aged gel; and (e) a step of burning the synthetic product, wherein step (e) includes a first burning step, in which burning is performed at a temperature of 70 to 200° C.; and a second burning step, in which burning is performed after the temperature is raised from a temperature range of 200° C. to 250° C. to a temperature range of 600 to 900° C.

For example, in the first burning step, temperature may be raised from a temperature range of 70 to 90° C. to a temperature range of 170 to 200° C., and then maintained at 170 to 200° C. for 4 to 8 hours to perform burning.

For example, in the first burning step, a heating rate may be 0.1 to 1° C./min.

For example, in the second burning step, the temperature may be raised from a temperature range of 200° C. to 250° C. to a temperature range of 630 to 900° C., and then maintained at 630 to 900° C. for 4 to 8 hours to perform burning.

For example, in the second burning step, a heating rate may be 0.5 to 1.5° C./min.

For example, the divalent cationic metal (A) may be one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co).

For example, the molar ratio (based on metal elements) of the trivalent cationic iron (Fe) precursor to the divalent cationic metal (A) precursor may be 1.5 to 3.0:1.0.

For example, the alcohol solvent may be one or more selected from methanol, ethanol, propanol, isopropanol, 1-butanol, and 2-butanol.

For example, the epoxide compound may be one or more selected from propylene oxide, ethylene oxide, and 1,2-epoxybutane.

For example, in step (c), aging of a gel may be performed at 10 to 40° C. for 12 to 48 hours.

For example, in step (d), drying may be performed at 70 to 100° C. for 12 to 48 hours.

For example, step (d) may include an alcohol exchange process.

For example, step (d) may include a filtering process.

In accordance with another aspect of the present invention, provided is a ferrite catalyst for oxidative dehydrogenation, wherein the ferrite catalyst has a carbon content of 0.3 to 0.4% by weight and a surface area of 10 to 12 m²/g, and is represented by Formula 1 below:

[Formula 1]

wherein A represents one or more selected from the group consisting of Cu, Ra, Ba, Sr, Ca, Be, Zn, Mg, Mn, and Co.

For example, the content of a spinel phase ferrite in the ferrite catalyst for oxidative dehydrogenation may be 99% by weight or more.

In accordance with yet another aspect of the present invention, provided is a method of preparing butadiene, wherein butadiene is prepared by oxidative dehydrogenation of reactants including butene, oxygen, nitrogen, and steam using the ferrite catalyst for oxidative dehydrogenation.

For example, when oxidative dehydrogenation is performed, a reaction temperature may be 300 to 600° C.

For example, in the reactants, a molar ratio of butene:oxygen:nitrogen:steam may be 1:0.1 to 6:1 to 10:1 to 20.

Advantageous Effects

As apparent from the foregoing, the present invention advantageously provides a ferrite catalyst for oxidative dehydrogenation and a method of preparing the ferrite catalyst. According to the present invention, when a ferrite catalyst for oxidative dehydrogenation is prepared, an epoxide-based sol-gel method is used. Accordingly, a pure spinel phase material that does not include an α-Fe₂O₃ phase can be obtained through simple processes, and the prepared ferrite catalyst has a large surface area and a macroporous structure. Thus, the ferrite catalyst of the present invention has higher reactivity than catalysts prepared by conventional methods.

BEST MODE

Hereinafter, the method of preparing a ferrite catalyst for oxidative dehydrogenation according to the present invention will be described in detail.

The present inventors confirmed that, when the reactivity of a catalyst prepared using an epoxide-based so-gel method was compared with the reactivity of a catalyst prepared using a conventional coprecipitation method, the catalyst prepared using an epoxide-based sol-gel method exhibited lower reactivity than the catalyst prepared using a conventional coprecipitation method. However, compared with the conventional coprecipitation method, several advantages were obtained when the sol-gel method was used. That is, a catalyst was prepared through simple processes, and the prepared catalyst did not contain an α-Fe₂O₃ phase. Based on these advantages, the present inventors conducted further studies.

As a result, it was found that a catalyst prepared by the sol-gel method contained a larger number of carbon atoms than a catalyst prepared by the conventional coprecipitation method, and thus had lower reactivity. Based on this result, the present inventors confirmed that a catalyst having increased reactivity was prepared when carbon content was reduced by controlling burning conditions. Based on these findings, the present invention was completed.

The method of preparing a ferrite catalyst for oxidative dehydrogenation according to the present invention includes (a) a step, in which a trivalent cationic iron (Fe) precursor and a divalent cationic metal (A) precursor are dissolved in an alcohol solvent to prepare a precursor solution; (b) a step, in which an epoxide compound is mixed with the precursor solution to obtain a gel; (c) a step of aging the obtained gel; (d) a step of obtaining a synthetic product by drying the aged gel; and (e) a step of burning the synthetic product, wherein step (e) includes a first burning step, in which burning is performed at a temperature of 70 to 200° C.; and a second burning step, in which burning is performed after temperature is raised from a temperature range of 200° C. to 250° C. to a temperature range of 600 to 900° C.

For example, in the first burning step, temperature may be raised from a temperature range of 70 to 90° C. to a temperature range of 170 to 200° C., and then maintained at 170 to 200° C. for 4 to 8 hours to perform burning. Within this range, a catalyst having a low carbon content and a large surface area and including 99% by weight or more of a spinel phase ferrite may be prepared.

As another example, in the first burning step, temperature may be raised from a temperature range of 75 to 85° C. to a temperature range of 185 to 200° C., and then maintained at 185 to 200° C. for 5 to 7 hours to perform burning. Within this range, a catalyst having a low carbon content and a large surface area and including 99% by weight or more of a spinel phase ferrite may be prepared.

As another example, in the first burning step, temperature may be raised from a temperature range of 80 to 85° C. to a temperature range of 195 to 200° C., and then maintained at 195 to 200° C. for 6 to 7 hours to perform burning. Within this range, a catalyst having a low carbon content and a large surface area and including 99% by weight or more of a spinel phase ferrite may be prepared.

For example, in the first burning step, a heating rate may be 0.1 to 1° C./min or 0.3 to 0.8° C./min, preferably 0.4 to 0.6° C./min. Within this range, a catalyst having a low carbon content and a large surface area may be prepared.

For example, the burning step may be performed under an air atmosphere using a conventional burning furnace.

For example, in the second burning step, the temperature may be raised from a temperature range of 200° C. to 250° C. to a temperature range of 630 to 900° C., and then maintained at 630 to 900° C. for 4 to 8 hours to perform burning. Within this range, a catalyst having a low carbon content and a large surface area may be prepared.

As another example, in the second burning step, the temperature may be raised from a temperature range of 200° C. to 230° C. to a temperature range of 640 to 870° C., and then maintained at 640 to 870° C. for 5 to 7 hours to perform burning. Within this range, a catalyst having a low carbon content and a large surface area may be prepared.

As another example, in the second burning step, the temperature may be raised from a temperature range of 200° C. to 220° C. to a temperature range of 645 to 855° C., and then maintained at 645 to 855° C. for 6 to 7 hours to perform burning. Within this range, a catalyst having a low carbon content and a large surface area may be prepared.

Preferably, in the second burning step, the temperature is raised from a temperature range of 200° C. to 220° C. to a temperature range of more than 700° C. to less than 800° C., and then maintained at more than 700° C. to less than 800° C. for 6 to 7 hours to perform burning. When butadiene is prepared using a catalyst prepared according to the conditions, conversion rate of butene and selectivity for 1,3-butadiene may be excellent.

For example, in the second burning step, a heating rate may be 0.5 to 1.5° C./min or 0.7 to 1.3° C./min, preferably 0.8 to 1.2° C./min. Within this range, a catalyst having a low carbon content and a large surface area may be prepared.

For example, the divalent cationic metal (A) may be one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), preferably zinc (Zn) or manganese (Mn), which exhibits particularly high activity in oxidative dehydrogenation of butene. Most preferably, the divalent cationic metal (A) is zinc (Zn) in terms of butadiene yield or selectivity for butadiene.

For example, each of the trivalent cationic iron (Fe) precursor and the divalent cationic metal (A) precursor may be one or more selected from the group consisting of nitrates, ammonium salts, sulfates, and chlorides, and is preferably selected from nitrates or chlorides. In this case, butadiene yield and selectivity for butadiene may be excellent.

For example, the molar ratio (based on metal elements) of the trivalent cationic iron (Fe) precursor to the divalent cationic metal (A) precursor may be 1.5 to 3.0:1.0 or 1.7 to 2.8:1.0, preferably 2.0 to 2.5:1.0. Within this range, a catalyst having a low carbon content and a large surface area may be prepared.

The alcohol solvent is not particularly limited as long as it is an alcohol solvent used in a conventional sol-gel method. For example, the alcohol solvent may be one or more selected from methanol, ethanol, propanol, isopropanol, 1-butanol, and 2-butanol, preferably ethanol. In this case, a catalyst having high reactivity may be prepared.

In addition, based on the total weight of the iron precursor and the alcohol solvent, the alcohol solvent may be contained in an amount of 85 to 98% by weight or 90 to % by weight, preferably 92 to 93% by weight or more. Within this range, the iron precursor and the divalent cationic metal (A) precursor may be completely dissolved and homogeneously dispersed, so that the desired effect of the present invention may be achieved.

In step (b), an epoxide compound may be added to the precursor solution of step (a) to generate a hydroxyl group in a hydrated divalent cationic metal, and at the same time, a gel may be obtained through condensation therebetween.

For example, the epoxide compound may be one or more selected from the group consisting of propylene oxide, ethylene oxide, and 1,2-epoxybutane, preferably propylene oxide. In this case, a catalyst having high reactivity may be prepared.

In addition, based on the total weight of the iron precursor and the epoxide compound, the epoxide compound may be contained in an amount of 67 to 82% by weight or 72 to 79% by weight, preferably 75 to 77% by weight or more. Within this range, a catalyst having high reactivity may be prepared.

Step (C) is performed to make the gel obtained in step (b) stronger and harder, so that a network structure grows.

For example, in step (c), aging may be performed at 10 to 40° C. or 15 to 35° C., preferably 20 to 30° C., for 12 to hours or 18 to 36 hours, preferably 20 to 26 hours. Within this range, a catalyst having high reactivity may be prepared.

In step (d) of obtaining a synthetic product by drying the aged gel, the alcohol solvent is removed from the aged gel. In general, in step (d), a temperature, at which the alcohol solvent evaporates, may be set to the lower limit temperature, and a temperature, at which a sample is changed, may be set to the upper limit temperature. In addition, drying time may be determined within a time range, within which the alcohol solvent is completely removed from the sample.

For example, in step (d), drying may be performed at 70 to 100° C. for 12 to 48 hours.

As another example, in step (d), drying may be performed at 75 to 90° C., preferably 75 to 85° C., for 18 to 36 hours, preferably 20 to 26 hours. Within this range, the aged gel may be sufficiently dried, and a stable structure may be formed.

For example, step (d) may include an alcohol exchange process.

In the alcohol exchange process, the alcohol solvent is additionally added to the aged gel obtained in step (c), and then the alcohol solvent is removed. Specifically, 1-chloro-2-propanol and the like, which are generated during formation of a gel and are present in a network structure, are removed, and the interior of the structure is filled with the alcohol solvent, so that collapse of the network structure is suppressed. Thus, a catalyst having high reactivity may be prepared.

The alcohol solvent may be additionally added in an amount of 500 to 2,000 parts by weight or 700 to 1,500 parts by weight, preferably 700 to 1,000 parts by weight based on 100 parts by weight of the gel obtained in step (c). Within this range, a catalyst having high reactivity may be prepared.

In addition, to allow the alcohol exchange process to proceed sufficiently, after the alcohol solvent is additionally added, the mixture of the alcohol solvent and the aged gel may be allowed to stand for 2 to 10 hours or 3 to 8 hours, preferably 5 to 6 hours.

Removal of the alcohol solvent may be performed without particular limitation. For example, after the standing step is performed, the synthetic product remains in a solid gel state and is in a state of being separated from the alcohol solvent. Thus, the alcohol solvent may be removed by pouring the alcohol solvent into a separate container.

The alcohol exchange process may be repeated one or more times or one to four times, preferably one to three times. Within this range, a catalyst having high reactivity may be prepared.

For example, step (d) may include a filtering process.

In the filtering process, a solution contained in the synthetic product is removed as much as possible before drying. Any conventional filtration method may be used in the filtering process without limitation. For example, a vacuum filtration method may be used.

For example, according to the vacuum filtration method, filtration may be performed under conditions wherein pressure is reduced to 100 to 300 mbar or 130 to 270 mbar, preferably 160 to 250 mbar. Within this range, a catalyst having high reactivity may be prepared.

As a specific example, in step (d), the gel aged in step (c) may be subjected to the alcohol exchange process and the filtering process, and then dried. In this case, a catalyst having high reactivity may be prepared.

In addition, the present invention provides a ferrite catalyst for oxidative dehydrogenation represented by Formula 1 below:

$$AFe_2O_4,\qquad\text{[Formula 1]}$$

wherein A represents Cu, Ra, Ba, Sr, Ca, Be, Zn, Mg, Mn, or Co.

For example, the ferrite catalyst may have a carbon content of 0.2 to 0.8% by weight and a surface area of 5 to 15 m$^2$/g.

For example, the ferrite catalyst may have a carbon content of 0.2 to 0.7% by weight or 0.3 to 0.4% by weight, preferably 0.3% by weight or more and less than 0.4% by weight. Within this range, the catalyst may have high reactivity.

In addition, the ferrite catalyst may have a surface area of, e.g., 7 to 13 m$^2$/g or 10 to 12 m$^2$/g, preferably 10 m$^2$/g or more and less than 12 m$^2$/g. Within this range, the catalyst may have high reactivity.

For example, the content of a spinel phase ferrite in the ferrite catalyst for oxidative dehydrogenation may be 99% by weight or more.

As another example, the content of a spinel phase ferrite in the ferrite catalyst may be 99.5% by weight or more, preferably 99.9 to 100% by weight.

Therefore, according to the present invention, a pure spinel phase catalyst that does not include an α-Fe$_2$O$_3$ phase may be obtained.

In the present invention, the contents of a spinel phase ferrite and α-Fe$_2$O$_3$ may be measured using X-ray diffraction analysis.

In addition, the present invention provides a method of preparing butadiene, wherein butadiene is prepared by oxidative dehydrogenation of reactants including butene, oxygen, nitrogen, and steam using the ferrite catalyst for oxidative dehydrogenation.

For example, the method of preparing butadiene according to the present invention may include an oxidative dehydrogenation step, in which oxidative dehydrogenation is performed while passing reactants including butene and oxygen through a reactor filled with the catalyst for oxidative dehydrogenation according to the present invention.

As a specific example, the method of preparing butadiene according to the present invention may include i) a step of filling a reactor with a catalyst for oxidative dehydrogenation; and ii) a step of performing oxidative dehydrogenation while continuously passing reactants including butene and oxygen into a catalyst layer present in the reactor filled with the catalyst.

The reactants may further include one or more selected from air, nitrogen, steam, and carbon dioxide.

In addition, in the case of butene, for example, 40 to 70% by weight of trans-2-butene and 30 to 60% by weight of cis-2-butene, or 50 to 65% by weight of trans-2-butene and 35 to 50% by weight of cis-2-butene, preferably 55 to 65% by weight of trans-2-butene and 35 to 55% by weight of cis-2-butene, may be included in the reactants. Within this range, conversion rate of butene, selectivity for butadiene, and butadiene yield may be excellent, so that butadiene may be effectively prepared.

For example, when oxidative dehydrogenation is performed, a reaction temperature may be 300 to 600° C. or 350 to 550° C., preferably 375 to 500° C. Within this range, conversion rate of butene, selectivity for butadiene, and butadiene yield may be excellent, so that butadiene may be effectively prepared.

For example, in the reactants, a molar ratio of butene:oxygen:nitrogen:steam may be 1:0.1 to 6:1 to 10:1 to 20. Within this range, reaction heat may be easily controlled, and butadiene yield may be excellent.

Specifically, in the reactants, a molar of butene:oxygen:nitrogen:steam may be 1:0.1 to 4:1 to 6:3 to 15, or 1:0.5 to 3:2 to 5:4 to 13, preferably 1:0.5 to 2:2 to 5:4 to 6. Within this range, operation stability and selectivity may be excellent.

For example, when oxidative dehydrogenation is performed, a gas hourly space velocity (GHSV) may be 20 to 300 h$^{-1}$ or 100 to 300 h$^{-1}$, preferably 250 to 300 h$^{-1}$ based on butene. Within this range, conversion rate and selectivity may be increased.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

EXAMPLE

Preparation of Ferrite Catalyst 62.303 g of FeCl$_3$6H$_2$O and 15.711 g of ZnCl$_2$ were added to 978.1 ml of ethanol, and the precursors were completely dissolved to obtain a precursor solution. Thereafter, while the precursor solution was stirred, 196.8 g of propylene oxide was fed into the precursor solution to convert the precursor solution into a gel. The gel-type synthetic product was aged for one day, and then the aged synthetic product was subjected to an ethanol exchange process twice. At this time, a solution generated upon gel formation was removed, and fresh ethanol was supplied to the synthetic product. In one of two ethanol exchange procedures, the synthetic product was allowed to stand for 6 hours after ethanol was supplied so that ethanol exchange could sufficiently proceed. The ethanol-exchanged synthetic product was filtered using vacuum filtration and dried in an oven at 80° C. for 24 hours. The dried synthetic product was subjected to burning in an air atmosphere (1 L/min) under various burning conditions as described below to prepare a catalyst.

Example 1

When a ferrite catalyst was prepared, burning was started at 80° C., the temperature was raised to 200° C. at a rate of 0.5° C./min, and then maintained at 200° C. for 6 hours. Thereafter, the temperature was raised from 200° C. to 650° C. at a rate of 1° C./min, and then maintained at 650° C. for 6 hours. In this case, the content of a spinel phase ferrite in the prepared ferrite catalyst was 100% by weight.

Example 2

Except that temperature was raised from 200° C. to 700° C. at a rate of 1° C./min, unlike in Example 1, in which temperature was raised from 200° C. to 650° C. at a rate of 1° C./min, a catalyst was prepared in the same manner as in Example 1. In this case, the content of a spinel phase ferrite in the prepared ferrite catalyst was 100% by weight.

Example 3

Except that temperature was raised from 200° C. to 750° C. at a rate of 1° C./min, unlike in Example 1, in which temperature was raised from 200° C. to 650° C. at a rate of 1° C./min, a catalyst was prepared in the same manner as in Example 1. In this case, the content of a spinel phase ferrite in the prepared ferrite catalyst was 100% by weight.

Example 4

Except that temperature was raised from 200° C. to 800° C. at a rate of 1° C./min, unlike in Example 1, in which temperature was raised from 200° C. to 650° C. at a rate of 1° C./min, a catalyst was prepared in the same manner as in Example 1. In this case, the content of a spinel phase ferrite in the prepared ferrite catalyst was 100% by weight.

Example 5

Except that temperature was raised from 200° C. to 850° C. at a rate of 1° C./min, unlike in Example 1, in which temperature was raised from 200° C. to 650° C. at a rate of 1° C./min, a catalyst was prepared in the same manner as in Example 1. In this case, the content of a spinel phase ferrite in the prepared ferrite catalyst was 100% by weight.

Comparative Example 1

When a ferrite catalyst was prepared, burning was started at 80° C., the temperature was raised to 650° C. at a rate of 1° C./min, and then maintained at 650° C. for 6 hours. In this case, the content of a spinel phase ferrite in the prepared ferrite catalyst was 100% by weight.

Comparative Example 2

When a ferrite catalyst was prepared, burning was started at 80° C., the temperature was raised to 200° C. at a rate of 0.5° C./min, and then maintained at 200° C. for 3 hours.

Thereafter, the temperature was raised from 200° C. to 300° C. at a rate of 0.5° C./min, and then maintained at 300° C. for 3 hours. Then, the temperature was raised from 300° C. to 650° C. at a rate of 1° C./min, and then maintained at 650° C. for 6 hours. In this case, the content of a spinel phase ferrite in the prepared ferrite catalyst was 100% by weight.

Comparative Example 3

When a ferrite catalyst was prepared, burning was started at 80° C., the temperature was raised to 200° C. at a rate of 0.5° C./min, and then maintained at 200° C. for 3 hours.

Thereafter, the temperature was raised from 200° C. to 300° C. at a rate of 0.5° C./min, and then maintained at 300° C. for 3 hours. Then, the temperature was raised from 300° C. to 550° C. at a rate of 1 C/min, and then maintained at 550° C. for 6 hours. In this case, the content of a spinel phase ferrite in the prepared ferrite catalyst was 100% by weight.

Comparative Example 4

When a ferrite catalyst was prepared, burning was started at 80° C., the temperature was raised to 200° C. at a rate of 0.5° C./min, and then maintained at 200° C. for 6 hours.

Thereafter, the temperature was raised from 200° C. to 550° C. at a rate of 1° C./min, and then maintained at 550° C. for 6 hours. In this case, the content of a spinel phase ferrite in the prepared ferrite catalyst was 100% by weight.

Comparative Example 5

47.667 g of a $FeCl_3 6H_2O$ precursor and 2.019 g of a $ZnCl_3$ precursor were dissolved in 835.5 g of distilled water to prepare a precursor solution. The precursor solution and aqueous ammonia were simultaneously dropped into 8,500 g of distilled water to obtain a synthetic product. At this time, pH was adjusted to 9. The synthetic product was subjected to a filtering process, and then dried in an oven at 90° C. Then, burning was performed in an air atmosphere (1 L/min). The burning reaction was started at 80° C., the temperature was raised to 650° C. at a rate of 1° C./min, and then maintained at 650° C. for 6 hours to prepare a catalyst. In this case, the content of a spinel phase ferrite in the prepared ferrite catalyst was 7.7% by weight.

The surface area and carbon content of each of catalysts prepared according to Example 1 and Comparative Examples 1 to 5 were measured by the following methods, and the obtained results are shown in Table 1.

Surface area ($m^2/g$): Surface area was measured using specific surface area analysis equipment (using nitrogen isothermal adsorption/desorption).

Carbon content (% by weight): Carbon content was measured using a thermogravimetric analyzer (TGA) under an oxygen atmosphere.

TABLE 1

| Burning conditions | Step | Surface area ($m^2/g$) | Carbon content (wt %) |
|---|---|---|---|
| Example 1 | 80 → 200° C., 0.5° C./min, 6 h maintenance<br>200 → 650° C., 1° C./min, 6 h maintenance | 10.96 | 0.3 |
| Comparative Example 1 | 80 → 650° C., 1° C./min, 6 h maintenance | 9.19 | 0.3 |
| Comparative Example 2 | 80 → 200° C., 0.5° C./min, 3 h maintenance<br>200 → 300° C., 0.5° C./min, 3 h maintenance<br>300 → 650° C., 1° C./min, 6 h maintenance | 11.16 | 0.4 |
| Comparative Example 3 | 80 → 200° C., 0.5° C./min, 3 h maintenance<br>200 → 300° C., 0.5° C./min, 3 h maintenance<br>300 → 550° C., 1° C./min, 6 h maintenance | 19.1 | 0.9 |
| Comparative Example 4 | 80 → 200° C., 0.5° C./min, 6 h maintenance<br>200 → 550° C., 1° C./min, 6 h maintenance | 19.09 | 0.9 |
| Comparative Example 5 | 80 → 650° C., 1° C./min, 6 h maintenance | 4.91 | 0.3 |

As shown in Table 1, compared with Comparative Example 5, in which a catalyst is prepared using a coprecipitation method, in the case of Example 1, in which a sol-gel method is used and burning is performed according to the conditions wherein temperature is raised from 80° C. to 200° C., maintained at 200° C. for 6 hours, raised from 200° C. to 650° C., and maintained at 650° C. for 6 hours, it can be confirmed that the surface area is wide while maintaining the carbon content (%) at the same level.

In addition, compared with Comparative Examples 1 to 4, in which a catalyst is prepared by a sol-gel method and burning conditions other than the burning conditions used in Example 1 are used, in the case of Example 1, it can be confirmed that the carbon content is low and the surface area is wide.

Figure 1:
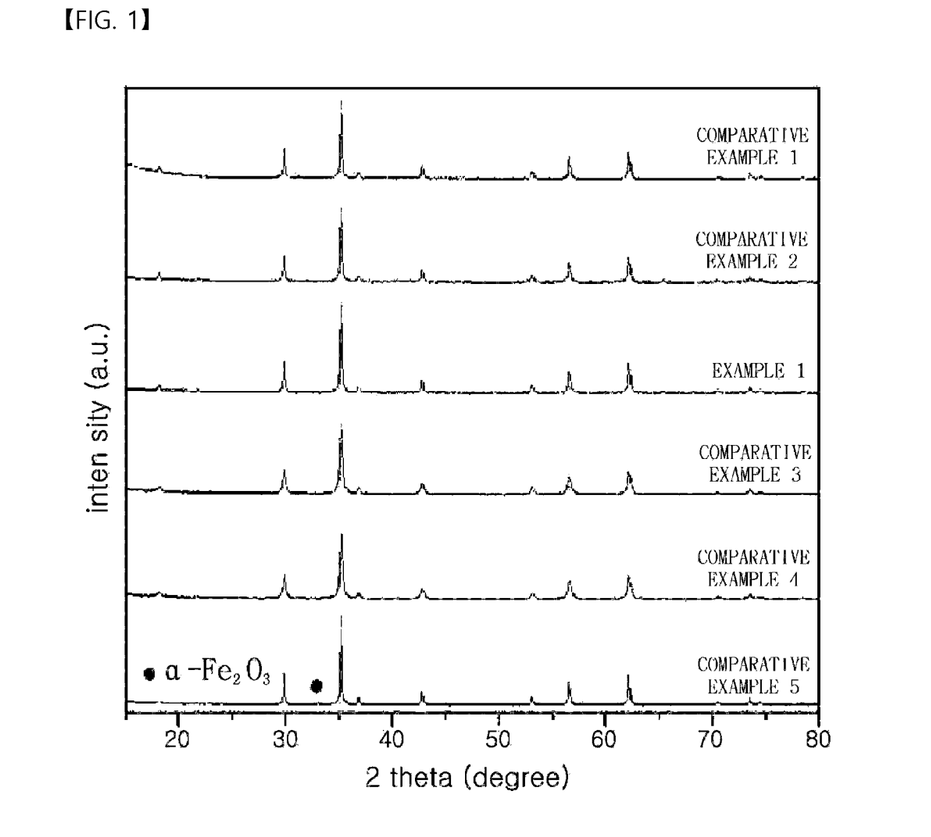
FIG. 1 is a graph showing X-ray diffraction spectra of the catalysts prepared according to Example 1 and Comparative Examples 1 to 5.

In addition, as shown in FIG. 1, in the cases of Example 1 and Comparative Examples 1 to 4, in which a sol-gel method is used, only a $ZnFe_2O_4$ phase is formed. In the case of Comparative Example 5, in which a coprecipitation method is used, an α-Fe$_2$O$_3$ phase and a ZnFe$_2$O$_4$ phase are simultaneously formed.

Test Example

Butadiene was prepared using the catalysts for oxidative dehydrogenation prepared according to Examples 1 to 5 and Comparative Example 5 using the following methods, and the obtained results are shown in Table 2.

Method of Preparing Butadiene

A mixture containing 60% by weight of trans-2-butene and 40% by weight of cis-2-butene and oxygen were used as reactants. In addition, nitrogen and steam were introduced into a reactor together with the reactants. A metal tubular reactor was used as the reactor. In the reactants, ratios of oxygen/butene, steam/butene, and nitrogen/butene were 1, 5, and 4, respectively. A gas hourly space velocity (GHSV) was set to 262 h$^{-1}$. A fixed bed reactor was filled with each of the catalysts prepared according to Examples and Comparative Examples. The volume of a catalyst layer contacting the reactants was fixed to 0.1 cc. For steam generation, water was injected, and water was vaporized at 150° C. using a vaporizer to generate steam. The generated steam was mixed with the butene mixture and oxygen contained in the reactants, and then introduced into the reactor. The amount of the butene mixture was controlled using a liquid mass flow controller, and the amounts of oxygen and nitrogen were controlled using a gas mass flow controller, and the injection rate of steam was controlled using a liquid pump. Reaction temperature was maintained at 375° C., 400° C., 425° C., 450° C., 475° C., or 500° C. After reaction, products were analyzed using a gas chromatography (GC). The results obtained from gas chromatography analysis were substituted into Equation 1 and 2 below to calculate the conversion rate of the butene mixture, the conversion rate of each of butene species contained in the mixture, and selectivity for 1,3-butadiene.

Conversion rate (%)=(Number of moles of butene reacted/number of moles of butene supplied)×100   [Equation 1]

Selectivity (%)=(Number of moles of 1,3-butadiene generated or number of moles of COx/number of moles of butene reacted)×100   [Equation 2]

TABLE 2

| Classification | Final burning temperature (° C.) | 375° C. | | 400° C. | | 425° C. | |
|---|---|---|---|---|---|---|---|
| | | Conversion rate (%) | Selectivity (%) | Conversion rate (%) | Selectivity (%) | Conversion rate (%) | Selectivity (%) |
| Example 1 | 650 | 68.7 | 86.4 | 52.4 | 76.9 | 40.7 | 67.8 |
| Example 2 | 700 | 80.5 | 92.5 | 71.8 | 87.3 | 68.8 | 86.1 |
| Example 3 | 750 | 87.6 | 92.2 | 83.4 | 92.1 | 76.0 | 88.5 |
| Example 4 | 800 | 78.7 | 89.9 | 69.4 | 85.9 | 63.2 | 82.7 |
| Example 5 | 850 | 77.7 | 90.4 | 71.6 | 86.5 | 71.8 | 85.4 |
| Comparative Example 5 | 650 | 70.0 | 88.5 | 71.0 | 88.6 | 72.6 | 87.8 |

TABLE 3

| Classification | Final burning temperature (° C.) | 450° C. | | 475° C. | | 500° C. | |
|---|---|---|---|---|---|---|---|
| | | Conversion rate (%) | Selectivity (%) | Conversion rate (%) | Selectivity (%) | Conversion rate (%) | Selectivity (%) |
| Example 1 | 650 | 38.9 | 68.3 | 32.8 | 62.1 | 29.5 | 56.6 |
| Example 2 | 700 | 64.8 | 84.0 | 61.3 | 82.1 | 59.3 | 80.9 |
| Example 3 | 750 | 73.2 | 86.7 | 68.8 | 82.2 | 65.5 | 79.9 |
| Example 4 | 800 | 59.1 | 81.5 | 56.1 | 78.6 | 53.2 | 76.3 |
| Example 5 | 850 | 67.9 | 83.2 | 64.9 | 81.0 | 62.3 | 78.1 |
| Comparative Example 5 | 650 | 69.6 | 85.2 | 65.4 | 80.7 | 63.8 | 77.6 |

As shown in Tables 2 and 3, compared with Comparative Example 5, in which a catalyst prepared using a conventional coprecipitation method is used, in the cases of Examples 1 to 5, the conversion rate and selectivity are equal to or better than those of Comparative Example 5 at a reaction temperature of 375 to 500° C.

In particular, in the case of Example 3, in which a final burning temperature is 750° C., the conversion and selectivity are higher than those of Comparative Example 5 at all reaction temperatures.

Figure 2:
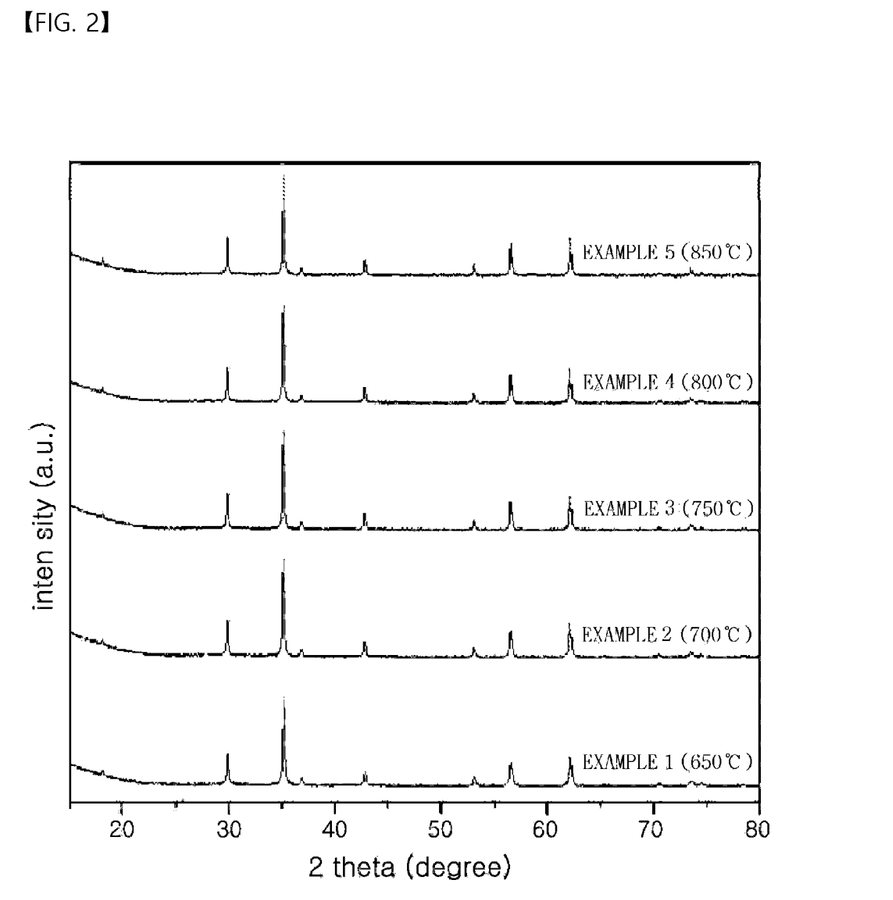
FIG. 2 is a graph showing X-ray diffraction spectra of the catalysts prepared according to Examples 1 to 5.

In addition, as shown in FIG. 2, as a result of XRD analysis of catalysts prepared at different burning temperatures based on Example 1 of the present invention, it can be confirmed that, as the burning temperature is changed, crystallinity of the catalyst is increased and the crystal structure of the catalyst does not change.

The invention claimed is:

1. A method of preparing a ferrite catalyst for oxidative dehydrogenation, comprising:
   (a) dissolving a trivalent cationic iron (Fe) precursor and a divalent cationic metal (A) precursor in an alcohol solvent to prepare a precursor solution;
   (b) mixing an epoxide compound with the precursor solution to obtain a gel;
   (c) aging the gel to form an aged gel;
   (d) drying the aged gel to obtain a synthetic product; and
   (e) burning the synthetic product, comprising:
      a first burning performed at a temperature of 70 to 200° C.; and
      a second burning performed after the temperature is raised from a temperature in the range of more than 200° C. to 250° C. to a temperature in the range of 600 to 900° C.

2. The method according to claim 1, wherein, in the first burning, the temperature is raised from a temperature in the range of 70 to 90° C. to a temperature in the range of 170 to 200° C., and then maintained at 170 to 200° C. for 4 to 8 hours.

3. The method according to claim 2, wherein, in the first burning, a heating rate is 0.1 to 1° C./min.

4. The method according to claim 1, wherein, in the second burning, the temperature is raised from a temperature in the range of more than 200° C. to 250° C. to a temperature in the range of 630° C. to 900° C., and then maintained at 630° C. to 900° C. for 4 to 8 hours.

5. The method according to claim 4, wherein, in the second burning, a heating rate is 0.5 to 1.5° C./min.

6. The method according to claim 1, wherein the divalent cationic metal (A) is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co).

7. The method according to claim 1, wherein a molar ratio, (based on metal element) of the trivalent cationic iron (Fe) precursor to the divalent cationic metal (A) precursor is 1.5 to 3.0:1.0.

8. The method according to claim 1, wherein the alcohol solvent is one or more selected from the group consisting of methanol, ethanol, propanol, isopropanol, 1-butanol, and 2-butanol.

9. The method according to claim 1, wherein the epoxide compound is one or more selected from the group consisting of propylene oxide, ethylene oxide, and 1,2-epoxybutane.

10. The method according to claim 1, wherein, in (c), the aging of the gel is performed at 10 to 40° C. for 12 to 48 hours.

11. The method according to claim 1, wherein, in (d), the drying is performed at 70 to 100° C. for 12 to 48 hours.

12. The method according to claim 1, wherein (d) further comprises an alcohol exchange process.

13. The method according to claim 1, wherein (d) further comprises a filtering process.

* * * * *